US009433206B2

(12) United States Patent
Kirby et al.

(10) Patent No.: US 9,433,206 B2
(45) Date of Patent: Sep. 6, 2016

(54) REDUCED FOAM DISPERSIONS AND FORMULATIONS THEREFOR

(75) Inventors: Andrew F. Kirby, Footscray (AU); Alice Lavranos, Mount Waverley (AU)

(73) Assignee: HUNTSMAN CORPORATION AUSTRALIA PTY LIMITED, Brooklyn (AU)

( * ) Notice: Subject to any disclaimer, the term of this patent is extended or adjusted under 35 U.S.C. 154(b) by 2866 days.

(21) Appl. No.: 11/722,912

(22) PCT Filed: Dec. 27, 2005

(86) PCT No.: PCT/US2005/047124
§ 371 (c)(1),
(2), (4) Date: Jun. 27, 2007

(87) PCT Pub. No.: WO2006/071887
PCT Pub. Date: Jul. 6, 2006

(65) Prior Publication Data
US 2008/0220972 A1 Sep. 11, 2008

Related U.S. Application Data

(60) Provisional application No. 60/639,849, filed on Dec. 27, 2004.

(30) Foreign Application Priority Data

May 25, 2005 (AU) ................ 2005902689

(51) Int. Cl.
| *A01N 25/00* | (2006.01) |
| *A01N 43/707* | (2006.01) |
| *A61K 9/14* | (2006.01) |
| *A01N 25/12* | (2006.01) |
| *A01N 25/14* | (2006.01) |
| *A01N 43/70* | (2006.01) |

(52) U.S. Cl.
CPC ............... *A01N 25/12* (2013.01); *A01N 25/14* (2013.01); *A01N 43/70* (2013.01)

(58) Field of Classification Search
None
See application file for complete search history.

(56) References Cited

U.S. PATENT DOCUMENTS

| 5,424,270 A | 6/1995 | Winston |
| 5,432,146 A | 7/1995 | Winston |
| 5,464,805 A | 11/1995 | Winston |
| 5,668,086 A | 9/1997 | Tadayuki et al. |
| 2001/0029240 A1 | 10/2001 | Hasebe et al. |
| 2004/0038826 A1* | 2/2004 | Kurita et al. ................ 504/127 |

FOREIGN PATENT DOCUMENTS

| JP | 60041601 | * 3/1985 |
| JP | 60214701 | * 10/1985 |
| JP | 2006-011652 A | 1/2006 |
| JP | 2010-268332 A | 11/2010 |
| WO | WO 91/18508 A | 12/1991 |
| WO | 9325081 A1 | 12/1993 |
| WO | WO-9325081 A1 | 12/1993 |
| WO | WO 95/34200 A | 12/1995 |

* cited by examiner

*Primary Examiner* — Alton Pryor
(74) *Attorney, Agent, or Firm* — Huntsman International LLC

(57) ABSTRACT

A composition and method for dispersing an agriculturally active agent are disclosed. In an embodiment, a solid agrochemical formulation is disclosed. The solid agrochemical formulation comprises an agriculturally active agent, a fatty acid salt, and a chelating agent.

31 Claims, No Drawings

REDUCED FOAM DISPERSIONS AND FORMULATIONS THEREFOR

BACKGROUND OF THE INVENTION

1. Field of the Invention

The present invention relates to aqueous agricultural formulations exhibiting reduced foaming. In particular, the invention relates to the use of fatty acid salts in conjunction with a chelating agent in reducing foaming when dispersing agriculturally active ingredients in solid form, as well as compositions comprising fatty acid salts and chelating agents.

2. Background of the Invention

Formulations of agriculturally useful active ingredients can be delivered in a water dispersible solid form (solid agrochemical formulation), which may be sprayed for agricultural treatments after dilution. In particular, such formulations include water dispersible granules (WDG) and wettable powders (WP) of a solid active agent or a liquid active ingredient loaded onto a solid carrier, which can effect WDG and WP formulations. Some active ingredients that are ultimately soluble in a final dilution useful for spraying may require initial dispersion in water for dissolution to take effect. These particular examples of WDGs may be alternatively described as water soluble granules (WSG).

A further type of formulation of agriculturally useful active ingredients is to deliver solid particles pre-dispersed in an aqueous medium. Such formulations typically include the suspension concentrate (SC) formulation type.

In a WDG, the solid active ingredient itself or liquid ingredient in solid form after loading onto a solid carrier may be in an agglomerated form that must disperse fully back to its primary particle size and thereafter maintain a stable dispersion suitable for spraying. In the case of a WP, the formulation may remain as a powder form but may penetrate the water of dilution so as to be sprayable. In the case of a WSG of a water soluble active ingredient with water insoluble fillers, the active ingredient and fillers may also be in agglomerated form. In the case of the liquid SC formulation, the solid particles remain dispersed, and the formulation is typically readily dispersed into water with minimal agitation.

A drawback in the use of formulations that are based on the active ingredient in a solid dispersible form or a pre-dispersed form is the development of foaming during the agitation used in the dispersion and dilution process. Such foaming can lead to difficulties in the even spraying of the spray liquid. Further difficulties include a foam-over or spillage of the spray liquid from out of the top of the mixing vessel. In addition, the development of foam may require a farmer to wait a long time for the foam to subside before spraying or require the addition of possibly expensive and potentially destabilising tank-added defoaming agents such as those based on silicone oil emulsions. Thus, a low or reduced foam profile is a desirable feature of such formulations.

The occurrence of foaming in water dispersible formulations such as WDGs and WPs is normally a direct consequence of the presence of a surfactant wetting agent in the formulation. However, various other agents may also contribute to foam formation and stabilisation of foaming. Such agents may include surface active impurities in the active ingredients, the surfactant dispersing agent, very fine particle sized solids and any surfactants added as adjuvants. The active ingredient per se in fine particulate or powder form may also cause or contribute to the stabilization of foam.

Various attempts to produce lower foaming WP and WDG formulations have been made in the past. Such attempts include two approaches. In the first approach, the wetting agents described above are replaced with lower foaming wetting agents. Such wetting agents include alcohol alkoxylates, in which some of the ethoxylate has been mixed with propoxylate or acetylenic diol ethoxylates. Such formulations typically exhibit poor dispersion performance for the formulation. In some cases, since they are liquid, incorporation into a solid matrix limits their availability to act as suitable wetting agents.

In the second approach, well known defoaming agents are added to the formulation. Such additives include silicone based defoamers, perfluoroalkyl defoaming agents and acetylenic diols as defoaming agents. Usually, these additives either inhibit the effective dispersion of the formulation, or they are bound up so tightly in the solid matrix that their defoaming ability is not observed. Further, the hydrolytic and heat instability of some organosilicone defoamers causes them to decompose under the conditions used to prepare WDG and WP formulations.

One formulation additive that is known to reduce foam in these formulations without the expense of a reduction in dispersion ability is a soap such as the sodium salt of a fatty acid. Addition of soap solution to a dispersed formulation readily shows foam reduction. Unfortunately, the foam reduction of fatty acid salts when built-in to the formulation has been shown to be quite limited. It appears to occur mainly in soft water (e.g, calcium and magnesium ion free), whereas the standard tests assume the water is usually much harder. As well, for some of the best wetting agents, the foam reduction may be too slow to be noticeable to any degree. Thus, there exists an ongoing need for formulations with reduced foaming.

BRIEF SUMMARY OF SOME OF THE PREFERRED EMBODIMENTS

It has now been found that a fatty acid salt used in combination with a chelating agent can give reduced foam when incorporated into WDG (including WSG) or WP formulations, particularly those which include highly effective wetting agents.

In a first aspect, the invention provides a solid agrochemical formulation comprising an agriculturally active agent, a fatty acid salt and a chelating agent. Preferably the formulation is in the form of a WDG or a WP. In further preferred embodiments, the formulation further comprises a wetting agent.

In another aspect, the invention provides for the use of a fatty acid salt and a chelating agent in reducing foaming associated with dispersing an agriculturally active agent in solid form in water.

A further aspect of the invention provides a method for preparing an aqueous dispersion of an agriculturally active agent in solid form comprising the steps of: providing a combination of an agriculturally active agent in solid form with a fatty acid salt and a chelating agent; and dispersing said combination in water.

In certain embodiments of the invention, the fatty acid salt and chelating agent are formulated together with the agriculturally active agent and optionally other agriculturally acceptable inert formulation additives such as a wetting agent and a dispersing agent, to form a water dispersible granule or wettable powder.

In yet another aspect, the present invention provides a defoaming composition comprising a fatty acid salt and a chelating agent. The fatty acid salt and chelating agent are preferably present in a ratio such that the use of the defoaming composition in dispersing an agriculturally active agent in solid form in water results in reduced foaming when compared to use of the fatty acid salt alone. The defoaming composition may comprise one or more agriculturally acceptable inert formulation additives such as carriers or fillers.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

DETAILED DESCRIPTION OF THE PREFERRED EMBODIMENTS

In an embodiment, a composition comprises an agriculturally active agent, a fatty acid salt, and a chelating agent. In another embodiment, the composition comprises an agriculturally active agent, a fatty acid salt, a chelating agent, and a polyacid polymer. Without being limited by theory, such compositions may provide improved foam reduction dispersions of WP and WDG formulations. Further, without being limited by theory, such compositions provide reduced foaming in circumstances in which a wetting agent develops a high degree of foaming.

Agriculturally active agents include any chemical substance that adversely effects the longevity, reproductive capability, and/or growth or metabolic function of plants, insects, fungi, and/or other various phyla. In an embodiment, an agriculturally active agent includes without limitation herbicides (e.g., triazines, ureas and sulphonyl ureas), insecticides (e.g., imidacloprid, fipronil and synthetic pyrethroids), fungicides, biocides, molluscicides, algaicides, plant growth regulators, anthelmintics, rodenticides, nematocides, acaricides, amoebicides, protozoacides, crop safeners, adjuvants, or combinations thereof. Without limitation, examples of agriculturally active agents in granulated or powder form in agricultural applications include triazine herbicides such as simazine, atrazine, terbuthylazine, terbutryn, prometryn and ametryn; urea herbicides such as diuron and fluometron; sulphonyl urea herbicides such as chlorsulfuron, metsulfuron methyl, nicosulfuron and triasulfuron; sulphonanilide herbicides such as flumetsulam; organophosphate insecticides such as azinphos methyl, chlorpyrifos, sulprofos and azamethiphos; carbamate insecticides such as aldicarb, bendiocarb, carbaryl and fenobucarb (2-sec-butylphenyl methylcarbamate); synthetic pyrethroids such as bifenthrin; fungicides including chlorothalonil, dimethomorph, benomyl, carbendazim, mancozeb; triazoles such as hexaconazole and diniconazole; and acaricides such as propargite. Agriculturally active agents are disclosed in the Pesticide Dictionary (contained in the Farm Chemicals Handbook) and the British Crop Protection Society: Pesticides Manual, which are incorporated herein by reference in their entirety. In an embodiment, agriculturally active agents include triazine, urea, or combinations thereof. In another embodiment, agriculturally active agents include triazine, urea, or combinations thereof in a WDG or WP formulation. In some embodiments, agriculturally active agents include atrazine, simazine, or combinations thereof. It is to be understood that the compositions may include one or more than one agriculturally active agent.

As used herein, an "agriculturally active agent in solid form" refers to either a solid agriculturally active agent per se or, preferably, a solid or liquid agriculturally active agent formulated into a solid form such as a WDG (including WSG) or WP. For instance, in some embodiments, solid agrochemical formulations are in a WDG or WP form and include at least one agriculturally active agent, at least one fatty acid salt, at least one chelating agent (optionally at least one polyacid polymer).

The fatty acid salt may include any fatty acid suitable for use with an agriculturally active agent. In an embodiment, the fatty acid salts include $C_8$ to $C_{21}$ fatty acids, which may be saturated or unsaturated (e.g., one of more degrees of unsaturation such as cis and/or trans). Without limitation, examples of saturated fatty acids include $C_{12}$ (lauric acid), $C_{14}$ (myristic acid), $C_{16}$ (palmitic acid), and $C_{18}$ (stearic acid). Without limitation, examples of unsaturated fatty acids include $C_{18}$ (oleic acid and elaidic acid).

The fatty acid salts may include any suitable salts. Without limitation, examples of suitable salts include ammonium and alkyl amine salts (eg $NH_4^+$, $NHEt_3^+$), alkali metal (eg. $Li^+$, $Na^+$, $K^+$) and alkaline earth (eg. $Mg^{2+}$ and $Ca^{2+}$) salts, and trivalent metal salts (e.g., $Al^{3+}$). Without limitation, examples of suitable fatty acid salts include sodium stearate, sodium oleate, aluminum stearate, or combinations thereof.

In an embodiment, the composition comprises one or more chelating agents. A chelating agent refers to a substance of which molecules may form several coordinate bonds to a single metal ion. In an embodiment, the chelating agent is any molecule able to form several coordinate bonds to a single metal ion and compatible with the other components of the composition. In some embodiments, the chelating agent includes any agriculturally acceptable metal ion chelators. Examples of agriculturally acceptable metal ion chelators include without limitation ethylene diamine tetraacetic acid (EDTA) and its various salts and hydrates, such as $Na^+$, $Li^+$, $K^+$, $NH_4^+$, $Ca^{2+}$ and $Mg^{2+}$; gluconic acid such as sodium gluconate and salts thereof; and nitrilotriacetic acid (NTA) and diethylenetriamine pentaacetic acid (DTPA) either in free acid form in their various salt and hydrate forms such as $Na^+$, $Li^+$, $K^+$, $NH_4^+$, $Ca^{2+}$ and $Mg^{2+}$; any hydrates thereof; or combinations thereof. One preferred example is the free acid form of EDTA.

The composition may include a ratio of fatty acid salt to chelating agent that is effective to achieve a reduced foaming result when compared to the use of a fatty acid salt alone. Suitable ratios may be achieved by routine experimentation such as known to one of ordinary skill in the art and may include ratios in a weight or molar range of about 1:100 to about 100:1, alternatively about 1:50 to about 50:1, and alternatively about 1:25 to about 25:1. Preferred ratios include a range of about 1:10 to about 10:1, alternatively about 1:5 to about 5:1. For some formulations, the chelating agent is present in a molar or weight excess, for example, a ratio of fatty acid salt to chelating agent of about 1:1.5 to about 1:3, alternatively about 1:2 w/w.

Without being limited by theory, the level of the defoaming combination of fatty acid salt and chelating agent or "defoaming composition" in the composition may be limited by the desired active ingredient strength in the formulation. In some embodiments, the level of the defoaming combination of fatty acid salt and chelating agent in the composition may range from about 0.1% w/w to about 20% w/w, alternatively from about 0.8 to about 1.6% w/w, and alternatively about 2.0% w/w.

In an embodiment, the composition further comprises a polyacid polymer. It has been found that a polyacid polymer may further enhance the defoaming effect of the fatty acid salt and chelating agent. The polyacid polymers include polymers comprising monomer residues bearing an acid group (e.g., carboxylic, sulfonic or phosphonic) and include homopolymers of an acid monomer residue, particularly a carboxylic acid or carboxylic anhydride monomer, and copolymers of 2 or more such acid monomer residues. In addition, the polyacid polymers also include any agriculturally acceptable metal ion salts (such as $Na^+$, $Li^+$, $K^+$, $Mg^{2+}$, $Ca^{2+}$ and $Al^{3+}$) and/or any other agriculturally acceptable cation salts, such as ammonium (e.g., $NH_4^+$) and sulphonium salts of the polymer. Polyacid polymers may also include sulphonic and phosphonic acid derivatives of polystyrene and condensed polyphenols and polynaphthalenes, obtained either by polymerization of the acid derivatized aromatic monomer or polymerization of the aromatic monomer and subsequent acid derivatization. Examples of polyacid polymers include, without limitation, sodium polyacrylate, sodium polymethacrylate and mixed combinations (copolymers) of acrylic and methacrylic acid monomer residues and polymaleic acid (e.g., from maleic acid or maleic anhydride). In a preferred embodiment, the polyacid polymer is a polyacid polymer salt comprising sodium polyacrylate with an average molecular weight ranging from about 500-20,000 daltons, alternatively less than about 10,000 daltons, and alternatively from about 2,100-about 5,000 daltons, and further alternatively from about 2,100-about 3,500 daltons. In an alternative embodiment, the chelating agent is a polyacid polymer.

The ratio of polyacid polymer to a combination of fatty acid salt and chelating agent may range from about 1:50 to about 50:1, alternatively from about 1:3 to about 1:1, and alternatively about 1:1.2. Without being limited by theory, the polyacid polymer enhances the effect of the defoamer (e.g., combination of fatty acid salt and chelating agent) while not altering the pH of the diluted formulation. The polyacid polymer may also act as an effective dispersant for clay and other inert filling agents in some formulations.

The level of the defoaming combination of polyacid polymer together with the fatty acid salt and chelating agent combination may be from about 0.5 to about 20 wt. % of the composition, alternatively from about 1.2 to about 2.5 wt. % of the composition.

When the agriculturally active ingredient is formulated, such as into a WP, WDG, SC or WSG formulation, a wide variety of other components, agriculturally acceptable additives, may be used, including fillers and carriers, dispersants and wetting agents. Any suitable method for formulating agriculturally active agents into WP, WDG or WSG formulations may be used.

In some embodiments, the composition may also comprise a wetting agent. Without being limited by theory, the main function of the wetting agent in a WP is to allow the powder to penetrate the water and become dispersible. This in practice involves the expulsion of air from between the hydrophobic particles in the powder. In the case of a WDG, the role of the wetting agent is three-fold. Firstly, it allows the water used as the primary binding/agglomerating agent of the formulation to be evenly distributed before being partly removed during the drying stage. The second function is to aid the disintegration of the granule matrix to primary particle size by allowing water on dilution to penetrate into the air-filled pore spaces between bound particles. Thirdly, the wetting agents aids in the immersion of the solid granules into the water in order for the disintegration process to commence.

Wetting agents may include but are not limited to salts of alkylbenzene sulphonates, alkyl sulph(on)ates, mono and di-alkylsulphosuccinates, alkylnaphthalene sulphonates, lignin sulphonates, ether carboxylates, alkylethersulphates, and alkyletherphosphates. Also used are nonionic surfactants such as alkylpolysaccharides, alcohol ethoxylates and alkylphenol ethoxylates. Since many of these are in liquid form, they are often provided in a solid form by incorporation into a solid matrix. The wetting agent may be used in the formulation at a rate of about 1-3% w/w.

Non-limiting examples from the alkylpolysaccharide class of wetting agents are alkylpolyglucosides derived from reaction with glucose and a primary hydrocarbon alcohol. Even more preferred are the highly crystalline derivatives such as obtained from ECOTERIC AS 20 and ECOTERIC AS10 (of Huntsman Corporation Australia Pty Ltd). Non-limiting examples from the monoalkylsulphosuccinate class are sodium or potassium salts of cyclohexyl, iso-octyl and n-octyl sulphosuccinate. Non-limiting examples from the dialkylsulphosuccinate class are sodium or potassium salts of dicyclohexyl, diisooctyl and di-n-octyl sulphosuccinates. Non-limiting examples from the class of nonionic surfactants include TERIC 168 (commercially available from Huntsman Corporation Australia Pty Ltd) and those loaded onto insoluble porous silicate carriers such as TERIC 157 (commercially available from Huntsman Corporation Australia Pty Ltd). Non-limiting examples of wetting agents from the urea surfactant complexes are urea adducts of alcohol ethoxylate surfactants such as TERWET 7050 (of Huntsman Corporation Australia Pty Ltd). Non-limiting examples of the salts of alkylbenzene and alkyl sulph(on)ates include TERWET 1004 commercially available from Huntsman Corporation Australia Pty Ltd. As well as NANSA HS 80, EMPICOL LV, EMPCIOL LXS 95/S and NANSA LSS 495/H, which are commercially available from Huntsman LLC.

The formulation may further include surfactants as dispersing agents, which include but are not limited to salts of alkylnaphthalene sulphonate condensates, salts of alkylphenol condensates, salts of sulphonated lignins, salts of poly acid resin copolymers, salts of polyphenol formaldehyde resins, salts of polyarylether sulphates such as tristyrylphenolethoxylate sulphate salts, alkoxylated alkylphenols and alcohols as well as block copolymers of ethyleneoxide and propylene oxide. Other dispersants may include those described in WO 9918788 and WO 9918787, which are each incorporated herein by reference in their entirety.

The composition may also include other insoluble materials that may be used in agricultural applications such as fillers and carriers, for example, but not limited to, natural and synthetic silicates and silicate minerals, mineral oxides and hydroxides and also natural and synthetically derived organic materials. Such materials may be added as porous carriers, as moisture inhibition agents, to aid binding or agglomeration properties of a formulation and/or to fill a formulation to a convenient weight. Examples of such fillers may include natural silicates such as diatomaceous earth, synthetic precipitated silicas, clays such as kaolin, attapulgites and bentonites, also zeolites, titanium dioxide, iron oxides and hydroxides, aluminium oxides and hydroxides, amorphous and crystalline silica, diatomite, talc, mica, urea-formaldehyde and polyphenolic resins and calcium carbonate, ammonium sulphate, sodium tripolyphosphate, calcium phosphate, urea and sodium carbonate or organic materials such as bagasse, charcoal, or synthetic organic polymers.

The pH of the composition may influence the defoaming effect. The preferred pH range of the composition is about 4-9. Without being limited by theory, a pH outside this range may result in degradation of the active agents, and/or a decrease in defoaming may be observed. Further, without being limited by theory, if the pH is too low, certain dispersant types may no longer function effectively on dilution. A more preferred pH range is 5-8. A particularly preferred pH range is 6-7.

The compositions may have a defoaming effect in formulations such as WDG, WP, SC, a slow dispersing granule (GR), and WSG formulations and any other solid dispersible formulation types as may be classified from time to time by the Crop Life International organization. For instance, in an embodiment, a composition is a suspension concentrate formulation type (SC) comprising water, an agriculturally active agent, a fatty acid salt, a chelating agent (and optionally a polyacid polymer). For a SC formulation, the ratio of fatty acid salt to chelating agent may include any suitable ratio for agricultural formulations. In an embodiment, the ratio of fatty acid salt to chelating agent may range from about 1:20 to about 20:1, alternatively from about 1:1.5 to 1:3. The level of fatty acid salt and chelating agent in a SC formulation may range from about 0.1-20% w/w and alternatively from about 0.8-2.0% w/w.

A "combination" of components, may refer to an intimate mixture of components, optionally formulated together as a WDG, SC or WP, or merely placement of the respective components together in a dispersing or mixing vessel, or any other degree of admixture in between. Thus, for example, where the inventive methods for preparing an aqueous dispersion refer to providing and dispersing a combination, this can include providing all the components formulated together as a WDG, SC or WP, or the active agent formulated as a WDG, SC or WP and the fatty acid salt and chelating agent provided either as separate components or as a defoaming composition into the dispersing tank or vessel. Where at least one or more of the components are provided separately, they can be optionally first mixed together before dispersion, or alternatively, simply mixed during the dispersion process.

Dispersion of the formulation in an aqueous medium may be achieved by any suitable methods. For instance, the method may take into account the nature of the composition and compatibility with the components of the composition. In a preferred embodiment, the dispersion of the composition in an aqueous solution is conducted either by hand or with a minimum of mechanical agitation. Mechanical agitation may include stirring, mixing, blending and other suitable processes.

The composition may be provided as a discrete composition for use in dispersing an active agent in solid form, such as formulated into a WDG, SC or WP, or alternatively simply formulated together with the active ingredient.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

The invention will now be described with reference to the following non-limiting Examples which are included for the purpose of illustrating certain embodiments of the invention and are not intended to limit the generality hereinbefore described.

EXAMPLES

A standard foaming test developed by the Collaborative International Pesticides Analytical Council, (CIPAC) and described in Method MT 47.2 was used to measure the limits of acceptable foam for various active ingredient formulations as set by the Food and Agriculture Organisation of the United Nations, Rome (FAO). For the purposes of these examples and illustrating the invention, any improvement over a comparative formulation that does not contain the defoaming combination will be considered desirable. A more preferable foam level (e.g., considered acceptable for normal agricultural use) may vary depending on the type of formulation. For WDG and WP formulations of atrazine, and simazine as exemplified below, a foam height of less than 30 mm at 2 minutes after agitation is stopped, would be regarded as acceptable for normal agricultural use. For formulations of ametryn, a foam height of less than 40 mm at 2 minutes after agitation is stopped would be regarded as acceptable.

For the purposes of these examples, the foam height is reported as initial height after agitation is stopped, "Int.", the height after 1 minute "1 min," and the height after 2 minutes "2 mins." The foam developed may also be further described as being "stable" meaning no reduction in foam height over 5 minutes, or "unstable" in which the foam height continues to reduce.

The actual CIPAC test prescribes a 100 ml measuring cylinder with 40 mm clearance above the 100 ml mark. For this exercise, a cylinder with a 50 mm clearance was used to show wider differences between formulations. Any formulation reaching a reported level of 50 mm can be assumed to have reached maximum height. It cannot be ascertained whether or not such a formulation would continue to give an even higher foam height.

Also reported are the general dispersion properties of the formulations in order to show if the formulations are acceptable for common use. In the case of WDG formulations the necessary dispersion tests included are CIPAC MT 168-suspensibility and CIPAC MT-167 Wet Sieve retention. The standards required for these properties vary with each formulation and from place to place. For the purposes of practical use, a suspensibility result of 65% would be the minimum acceptable level and a wet sieve retention of <1% for a 53 micron sieve, and 0.1% for a 150 micron sieve would be minimum acceptable levels.

For WP formulations, a static wetting time test CIPAC MT 53.3.1 is additionally performed. A static wetting time of <1 minute would be considered as acceptable in the example formulations following. For an SC formulation, the desire is to have a formulation that does not show settling of the solid phase or any significant change in viscosity over time. These properties are also measured in the case of the SC formulations herein.

COMPARATIVE EXAMPLES

The results for persistent foaming and dispersion properties for the formulations of Comparative Examples 1-17 are reported in Table 1 following Comparative Example 17.

Comparative Example 1

An Atrazine 900 g/Kg WG formulation was made according to the following composition:

| Atrazine technical (98% w/w) | 918 g/Kg |
|---|---|
| TERSPERSE 2700 | 42 |
| TERSPERSE 2100 | 5 |
| TERWET 1004 | 16 |
| TALC T20A | 14 |
| Water (residual) | 5. |

The granule was made by first blending the solid ingredients by hand then co-milling them together in a laboratory powder mill. A quantity of water approximately 18% w/w was added while the powder was mixed under agitation. The partly wet powder was then extruded through a 1 mm screen on a laboratory scale basket type extruder. The strands extruded were broken to approximately uniform size by shaking and then dried in a fluid bed drier to a residual water content of approximately 0.5% w/w.

TERSPERSE 2700 is an acid resin copolymer based dispersing agent supplied by Huntsman Corporation Australia Pty Limited. TERSPERSE 2100 is a naphthalene sulphonate based dispersing agent supplied by Huntsman LLC. TERWET 1004 is an anionic surfactant wetting agent supplied by Huntsman Corporation Australia Pty Limited. TALC T20A a fine talc mineral filler and is supplied by Unimin Pty Ltd. The formulation exhibited an unacceptable level of foam.

Comparative Example 2

An Atrazine 900 g/Kg WG formulation was made according to the following composition:

| Atrazine technical (98% w/w) | 918 g/Kg |
|---|---|
| TERSPERSE 2700 | 42 |
| TERWET 1004 | 16 |
| TALC T20A | 10 |
| ANTIFOAM C on Tixosil | 10 |
| Water (residual) | 4. |

ANTIFOAM C is a silicone oil emulsion based defoaming agent from Dow Chemical. Tixosil is a silica carrier onto which the Antifoam C is adsorbed. The formulation exhibited an unacceptable level of foam.

Comparative Example 3

An Atrazine 900 g/Kg WG formulation was made according to the following composition:

| Atrazine technical (98% w/w) | 918 g/Kg |
|---|---|
| TERSPERSE 2700 | 42 |
| TERWET 1004 | 16 |
| TALC T20A | 10 |
| FLUOWET PL80 | 10 |
| Water (residual) | 4. |

FLUOWET PL80 is a product of Clariant AG and is a perfluoralkyl defoaming agent.

Whilst exhibiting an acceptable level of foam, the formulation exhibited an unacceptable level of dispersion performance.

Comparative Example 4

An Atrazine 900 g/Kg WG formulation was made according to the following composition:

| Atrazine technical (98% w/w) | 918 g/Kg |
|---|---|
| TERSPERSE 2700 | 37.5 |
| TERIC 168 | 12.5 |
| TALC T20A | 27 |
| Water (residual) | 5. |

TERIC 168 is an alcohol alkoxylate low foam wetting surfactant supplied by Huntsman Corporation Australia Pty Limited. The surfactant was added by dissolving it in the water added to the powder. The formulation exhibited an unacceptable level of foam.

Comparative Example 5

An Atrazine 900 g/Kg WG formulation was made according to the following composition:

| Atrazine technical. (97% w/w) | 927 g/Kg |
|---|---|
| TERSPERSE 2700 | 42 |
| TERWET 1004 | 15 |
| Stearic Acid | 5 |
| Starch Powder | 6 |

Water (residual) 5.
This formulation exhibited an unacceptable level of foam.

Comparative Example 6

A Simazine 900 g/Kg WG formulation was made according to the following composition:

| Simazine technical (98% w/w) | 918 g/Kg |
|---|---|
| TERSPERSE 2700 | 36 |
| TERWET 1004 | 16 |
| TALC T20A | 25 |
| Water (residual) | 5. |

The formulation exhibited an unacceptable level of foam.

Comparative Example 7

A Simazine 900 g/Kg WG formulation was made according to the following composition:

| Simazine technical. (98% w/w) | 918 g/Kg |
|---|---|
| TERSPERSE 2700 | 36 |
| SUPRAGIL WP | 16 |
| TALC T20A | 25 |
| Water (residual) | 5. |

SUPRAGIL WP is an alkylnaphthalene sulphonate based wetting agent from Rhodia Inc. The formulation exhibited an unacceptable level of foam.

Comparative Example 8

A Simazine 900 g/Kg WG formulation Was made according to the following composition:

| Simazine technical (98% w/w) | 918 g/Kg |
|---|---|
| TERSPERSE 2700 | 36 |
| EMPIMIN OT-50 | 32 |
| TALC T20A | 25 |
| Water (residual) | 5 |

EMPIMIN OT-50 is an approximately 50% w/w aqueous solution of a sulphosuccinate salt based wetting agent from Huntsman LLC. The surfactant was added by dissolving it in the water added to the powder. The water contained in EMPIMIN OT-50 was evaporated during the drying process. This formulation exhibited an unacceptable level of foam.

Comparative Example 9

A Simazine 900 g/Kg WG formulation was made according to the following composition:

| Simazine technical (98% w/w) | 918 g/Kg |
|---|---|
| TERSPERSE 2700 | 36 |
| TERWET 1004 | 16 |
| ANTIFOAM C | 5 |
| TALC T20A | 20 |
| WATER (residual) | 5. |

ANTIFOAM C is a silicone oil emulsion based defoaming agent from Dow Chemical. It was added to the formulation by mixing with the water added to the powder. The formulation exhibited an unacceptable level of foam.

Comparative Example 10

A simazine 900 g/Kg WG formulation was made according to the following composition:

| Simazine technical (98% w/w) | 918 g/Kg |
|---|---|
| TERSPERSE 2700 | 36 |
| TERWET 1004 | 16 |
| FLUOWET PL80 | 5 |
| TALC T20A | 20 |
| Water (residual) | 5. |

FLUOWET PL80 is a product of Clariant AG and is a perfluoralkyl defoaming agent. It was added to the formulation by mixing with the water added to the powder. Though the formulation exhibited an acceptable level of foam, it exhibited an unacceptable level of dispersion performance.

Comparative Example 11

A simazine 900 g/Kg WG formulation was made according to the following composition:

| Simazine technical (98% w/w) | 918 g/Kg |
|---|---|
| TERSPERSE 2700 | 36 |
| TERWET 1004 | 16 |
| Stearic Acid | 10 |
| Simazine technical (98% w/w) | 918 g/Kg |
| TALC T20A | 15 |
| Water (residual) | 5. |

The formulation exhibited an unacceptable level of foam.

Comparative Example 12

An Ametryn 800 g/Kg WG formulation was made according to the following composition:

| Ametryn technical (97% w/w) | 825 g/Kg |
|---|---|
| TERSPERSE 2700 | 50 |
| TERWET 1004 | 16 |
| DIATOMITE D30 | 87 |
| TALC T45B | 17 |
| Water(residual) | 5. |

DIATOMITE D30 is powdered diatomaceous earth commercially available from Unimin Pty Ltd. TALC T45B is a grade of talc also commercially available from Unimin Pty Ltd. The formulation exhibited an unacceptable level of foam.

Comparative Example 13

An atrazine 800 g/Kg wettable powder formulation was made with the following composition:

| Atrazine technical (97% w/w) | 825 g/kg |
|---|---|
| TERSPERSE 2425 | 30 |
| EMPICOL LXS 95/S | 20 |
| TALC T45-B | 12.5. |

The solid ingredients were blended together then milled in a laboratory powder mill.

TERSPERSE 2425 is an alkyl naphthalene sulphonate salt dispersant supplied by Huntsman LLC. EMPICOL LXS/95S is an alkylsulph(on)ate wetting agent supplied by Huntsman Corporation LLC. The formulation exhibited an unacceptable level of foam.

Comparative Example 14

An Ametryn 800 g/Kg wettable powder formulation was made with the following composition:

| Ametryn technical (98% w/w) | 842 g/kg |
|---|---|
| TERSPERSE 2425 | 30 |
| TERWET 1004 | 8 |
| EMPICOL LXS 95/S | 7 |
| TALC T45-B | 113. |

The solid ingredients were blended together then milled in a laboratory powder mill. The formulation exhibited an unacceptable level of foam.

Comparative Example 15

An Atrazine 900 g/Kg WG formulation was made according to the following composition:

| Atrazine technical. (98% w/w) | 918 g/Kg |
|---|---|
| TERSPERSE 2700 | 39 |
| TERSPERSE 2100 | 5 |
| TERWET 1004 | 15 |
| Sodium Stearate | 3.5 |
| AQUALIC DL 100 | 16.5 |
| Water (residual) | 3. |

The foam height (mm) results are shown in Table I. AQUALIC DL 100 is a sodium polyacrylate polymer of approximate molecular weight 3,500 commercial available from Nippon Shokubai Co Ltd. The foam was very stable. In this example, EDTA was replaced with more AQUALIC DL100 suggesting that if the DL100 was simply acting as another chelate and the defoaming effect was related to total amount chelate then this formulation would have shown good defoaming.

Comparative Example 16

An Atrazine 900 g/Kg WG formulation was made according to the following composition:

| Atrazine technical. (98% w/w) | 918 g/Kg |
|---|---|
| TERSPERSE 2425 | 60 |
| SUPRAGIL WP | 15 |
| Talc T20A | 2 |
| Water (residual) | 5. |

The results are shown in Table 1. The foam is highly stable.

Comparative Example 17

A metsulfuron 750 g/Kg WG formulation was made according to the following composition:

| Metsulfuron technical. (94% w/w) | 798 g/Kg |
|---|---|
| TERSPERSE 2700 | 45 |
| TERWET 1004 | 15 |
| TALC T20A | 20 |
| KINGWHITE 65 | 117 |
| Water (residual) | 5. |

KINGWHITE 65 is a grade of Kaolin clay available from Unimin Pty Limited. The results are shown in Table I. This foam was very stable.

TABLE 1

Comparative Example Results

| Comparative Example No. | Persistent Foaming (MT47.2) Mm | | | Suspensibility (MT 15.2) % | Wet Sieve Retention | | Static Wetting (MT 53.3.1) Time Secs. |
|---|---|---|---|---|---|---|---|
| | Int | 1 min | 2 min | | 150 um % | 53 um % | |
| 1 | 50 | 50 | 50 | 90 | 0.002 | 0.12 | |
| 2 | 50 | 42 | 40 | 91 | 0.31 | 1.44 | |
| 3 | 50 | 20 | 5 | 65 | 1.80 | 8.90 | |
| 4 | 45 | 40 | 40 | 89 | 0.020 | 1.76 | |
| 5 | 50 | 32 | 30 | 93* | 0.017 | 0.242 | |
| 6 | 50 | 50 | 50 | 97 | 0.0081 | 0.0036 | |
| 7 | 50 | 45 | 42 | 78 | 0.8 | 4.8 | |
| 8 | 40 | 30 | 30 | 97 | 0.005 | 0.092 | |
| 9 | 50 | 50 | 50 | 93 | 0.036 | 0.0420 | |
| 10 | 50 | 15 | 2 | 27.8 | 35.2 | 4.6 | |
| 11 | 42 | 42 | 40 | 96 | 0.0037 | 0.0248 | |
| 12 | 50 | 50 | 50 | 89 | 0.035 | 0.63 | |
| 13 | 50 | 50 | 50 | 72 | 0.47 | 1.98 | 120 |
| 14 | 50 | 50 | 50 | 80 | 0.015 | 0.33 | 15 |
| 15 | 45 | 40 | 40 | 50 | 2.0 | 13.4 | |
| 16 | 45 | 32 | 30 | 86 | 0.02 | 0.04 | |
| 17 | 47 | 40 | 40 | 81 | 0.08 | 1.02 | |

*Milled on hammer mill instead of normal lab mill. This usually results in a higher suspensibility due to finer milling.

Comparative Example 18

A 430 g/L tebuconazole SC formulation was made with the following composition.

| Tebuconazole technical (96%) | 44.79(g/L) |
|---|---|
| TERSPERSE 4894 | 40 |
| Monoethylene glycol | 50 |
| Silicone antifoam | 2 |
| Xanthan gum | 2 |
| PROXEL GXL | 1 |
| Water to 1 L. | |

The formulation was prepared by high shear mixing tebuconazole, TERSPERSE 489440, monoethylene glycol, silicone antifoam and water. TERSPERSE 4894 is a blend of nonionic surfactants that acts as a wetter and dispersant that is commercially available from Huntsman Corporation Australia Pty Limited. The mixture was then bead milled to a d(0.5) particle size of approximately 8 um. After milling, to the millbase was added xanthan gum (as 2% RHODOPOL 23 gel in water with 1% PROXEL GXL) and the formulation diluted with water to yield 430 g/L tebuconazole. RHODOPOL 23 is a xanthan gum commercially available from Rhodia Inc. PROXEL GXL 20 is a biocide commercially available from Avecia Inc. The results are presented in Table 2.

TABLE 2

Formulation performance before and after 2 weeks at 54° C. storage stability

|  | Initial | After 2 weeks at 54° C. |
|---|---|---|
| Appearance | Homogeneous white suspension. | White suspension. No hard packed layer. |
| Syneresis | Nil | 1%, excellent re-dispersion. |
| Viscosity (Brookfiled LV, spindle #2 at 30 rpm) (cPs) | 740 | 680 |
| Particle Size d(0.5) (μm) | 7.7 | 6.9 |
| Particle Size d(0.9) (μm) | 13.6 | 12.1 |
| Persistent foam (mm) | Int - 22, 1 min - 16, 2 min - 16 | N/A |

This level of foam is acceptable but it can be improved (see Embodiment Example 23).

The results for persistent foaming and dispersion properties for the formulations of Embodiment Examples 1-28 are reported in Table 3 following Embodiment Example 28.

Embodiment Example 1

An Atrazine 900 g/Kg WG formulation was made according to the following composition:

| Atrazine technical (98% w/w) | 918 g/Kg |
|---|---|
| TERSPERSE 2700 | 39 |
| TERSPERSE 2100 | 5 |
| TERWET 1004 | 15 |
| Sodium Stearate | 3.5 |
| EDTA (acid form) | 7.5 |
| AQUALIC DL 100 | 9 |
| Water (residual) | 3. |

AQUALIC DL 100 is the sodium salt of a polyacrylic acid copolymer from Nippon Shokubai Co Ltd. The formulation exhibited an acceptable and very low level of foam. This can be compared to the results obtained for Comparative Examples 1, 2, 4 and 5. The formulation also exhibited an acceptable level of dispersion performance compared to that of Comparative Example 3.

Embodiment Example 2

An Atrazine 900 g/Kg WG formulation was made according to the following composition:

| Atrazine technical. (98% w/w) | 918 g/Kg |
|---|---|
| TERSPERSE 2700 | 42 |
| TERWET 1004 | 15 |
| Sodium Stearate | 4 |
| EDTA (acid form) | 8 |
| TALC T20A | 8 |
| Water (residual) | 5. |

The formulation exhibited an acceptable and very low level of foam. This can be compared to the results obtained for Comparative Examples 1, 2, 4 and 5. The formulation also exhibited an acceptable level of dispersion performance compared to that of Comparative Example 3.

Embodiment Example 3

An Atrazine 900 g/Kg WG formulation was made according to the following composition:

| Atrazine technical (98% w/w) | 918 g/Kg |
|---|---|
| TERSPERSE 2700 | 42 |
| TERWET 1004 | 15 |
| Sodium Oleate | 4 |
| EDTA (acid form) | 8 |
| TALC T20A | 8 |
| Water (residual) | 5. |

The formulation exhibited an acceptable level of foam. This can be compared to the results obtained for Comparative Examples 1, 2, 4 and 5. The formulation also exhibited an acceptable level of dispersion performance compared to that of Comparative Example 3.

Embodiment Example 4

A simazine 900 g/Kg WG formulation was made according to the following composition:

| Simazine technical (98% w/w) | 918 g/Kg |
|---|---|
| TERSPERSE 2700 | 36 |
| TERWET 1004 | 16 |
| Sodium Stearate | 4 |
| EDTA (acid form) | 8 |
| TALC T20A | 13 |
| Water (residual) | 5. |

The formulation exhibited an acceptable level of foam. This can be compared to the results obtained for Comparative Example 6.

Embodiment Example 5

A simazine 900 g/Kg WG formulation was made according to the following composition:

| Simazine technical (98% w/w) | 918 g/Kg |
|---|---|
| TERSPERSE 2700 | 36 |
| TERWET 1004 | 16 |
| Sodium Stearate | 4 |
| EDTA (acid form) | 8 |
| AQUALIC DL 100 | 10 |
| TALC T20A | 3 |
| Water (residual) | 5. |

The formulation exhibited an acceptable and very low level of foam. This can be compared to the results obtained for Comparative Example 6 and is a further improvement on that of Embodiment Example 4.

Embodiment Example 6

A simazine 900 g/Kg WG formulation was made according to the following composition:

| Simazine technical (98% w/w) | 918 g/Kg |
|---|---|
| TERSPERSE 2700 | 36 |
| SUPRAGIL WP | 16 |
| Sodium Stearate | 4 |
| EDTA (acid form) | 8 |
| AQUALIC DL 100 | 10 |
| TALC T20A | 3 |
| WATER (residual) | 5. |

The formulation exhibited an acceptable level of foam and can be compared to that of Comparative Example 7.

Embodiment Example 7

A simazine 900 g/Kg WG formulation was made according to the following composition:

| Simazine technical (98% w/w) | 918 g/Kg |
|---|---|
| TERSPERSE 2700 | 36 |
| EMPIMIN OT-50 | 32 |
| Sodium Stearate | 4 |
| EDTA (acid form) | 8 |
| AQUALIC DL 100 | 10 |
| TALC T20A | 3 |
| Water (residual) | 5. |

The formulation exhibited an acceptable and very low level of foam and can be compared to that of Comparative Example 8.

Embodiment Example 8

A simazine 900 g/Kg WG formulation was made according to the following composition:

| Simazine technical (98% w/w) | 918 g/Kg |
|---|---|
| TERSPERSE 2700 | 36 |
| TERWET 1004 | 16 |
| Sodium Oleate | 4 |
| EDTA (acid form) | 8 |
| AQUALIC DL 100 | 10 |
| TALC T20A | 3 |
| Water (residual) | 5. |

The formulation exhibited a reduced of foam compared to that of Comparative Example 6.

Embodiment Example 9

A simazine 900 g/Kg WG formulation was made according to the following composition:

| Simazine technical. (98% w/w) | 918 g/Kg |
|---|---|
| TERSPERSE 2700 | 36 |
| TERWET 1004 | 16 |
| Sodium Laurate | 4 |
| EDTA (acid form) | 8 |
| AQUALIC DL 100 | 10 |
| TALC T20A | 3 |
| Water (residual) | 5. |

This formulation exhibited a reduced level of foam when compared to that of Comparative Example 6.

Embodiment Example 10

A simazine 900 g/Kg WG formulation was made according to the following composition:

| Simazine technical. (98% w/w) | 918 g/Kg |
|---|---|
| TERSPERSE 2700 | 36 |
| TERWET 1004 | 16 |
| Sodium Stearate | 4 |
| EDTA di-sodium salt | 10 |
| TALC T20A | 11 |
| Water (residual) | 5. |

This formulation exhibited a reduced level of foam compared to that of Comparative Example 6.

Embodiment Example 11

A simazine 900 g/Kg WG formulation was made according to the following composition:

| Simazine technical (98% w/w) | 918 g/Kg |
|---|---|
| TERSPERSE 2700 | 36 |
| TERWET 1004 | 16 |
| Sodium Stearate | 4 |
| NTA (acid form) | 8 |
| TALC T20A | 13 |
| Water (residual) | 5. |

This formulation now exhibited an acceptable level of foam and can be compared to that of Comparative Example 6.

Embodiment Example 12

A simazine 900 g/Kg WG formulation was made according to the following composition:

| Simazine technical (98% w/w) | 918 g/Kg |
|---|---|
| TERSPERSE 2700 | 36 |
| TERWET 1004 | 16 |
| Sodium Stearate | 4 |
| NTA (acid form) | 8 |
| AQUALIC DL 400 | 10 |
| TALC T20A | 3 |
| Water (residual) | 5. |

This formulation now exhibited a reduced level of foam compared to that of Comparative Example 6.

Embodiment Example 13

A simazine 900 g/Kg WG formulation was made according to the following composition:

| Simazine technical. (98% w/w) | 918 g/Kg |
|---|---|
| TERSPERSE 2700 | 36 |
| TERWET 1004 | 16 |
| Sodium Stearate | 4 |
| DEQUEST 2016 | 8 |
| AQUALIC DL 100 | 10 |
| TALC T20A | 3 |
| Water (residual) | 5. |

DEQUEST 2016 is the tetra sodium salt of hydroxyethylene 1,1-diphosphonic acid supplied by Monsanto Corp. This formulation exhibited a lower level of foam compared to that of Comparative Example 6.

Embodiment Example 14

A simazine 900 g/Kg WG formulation was made according to the following composition:

| Simazine technical (98% w/w) | 918 g/Kg |
| --- | --- |
| TERSPERSE 2700 | 36 |
| TERWET 1004 | 16 |
| Sodium Stearate | 4 |
| Oxalic acid | 8 |
| AQUALIC DL 100 | 10 |
| TALC T20A | 3 |
| Water (residual) | 5. |

This formulation exhibited a reduced level of foam compared to that of Comparative Example 6.

Embodiment Example 15

A simazine 900 g/Kg WG formulation was made according to the following composition:

| Simazine technical (98% w/w) | 918 g/Kg |
| --- | --- |
| TERSPERSE 2700 | 36 |
| TERWET 1004 | 16 |
| Sodium Stearate | 4 |
| EDTA (acid form) | 8 |
| Polyacrylic acid, sodium salt MW 2100 | 10 |
| TALC T20A | 3 |
| Water (residual) | 5. |

This formulation exhibited an acceptable and very low level of foam compared to that of Comparative Example 6.

Embodiment Example 16

A simazine 900 g/Kg WG formulation was made according to the following composition:

| Simazine technical (98% w/w) | 918 g/Kg |
| --- | --- |
| TERSPERSE 2700 | 36 |
| TERWET 1004 | 16 |
| Sodium Stearate | 4 |
| EDTA (Acid form) | 8 |
| Polyacrylic acid, sodium salt MW 5100 | 10 |
| TALC T20A | 3 |
| Water (residual) | 5. |

This formulation exhibited a reduced level of foam compared to that of Comparative Example 6.

Embodiment Example 17

A simazine 900 g/Kg WG formulation was made according to the following composition:

| Simazine technical. (98% w/w) | 918 g/Kg |
| --- | --- |
| TERSPERSE 2700 | 36 |
| TERWET 1004 | 16 |
| Sodium Stearate | 4 |
| EDTA (acid form) | 8 |
| Poly vinyl alcohol MW 20,000 | 10 |
| TALC T20A | 3 |
| Water (residual) | 5. |

This formulation exhibited a reduced level of foam compared to that of Comparative Example 6. The addition of a water-soluble non-polyacid polymer provided no improvement over Embodiment Example 4. The dispersion properties are also reduced and this is believed to be due to the presence of large particles of the PVA, which do not completely dissolve.

Embodiment Example 18

An Ametryn 800 g/Kg WG formulation was made according to the following composition:

| Ametryn technical (97% w/w) | 825 g/Kg |
| --- | --- |
| TERSPERSE 2700 | 50 |
| TERWET 1004 | 10 |
| Sodium Stearate | 5 |
| EDTA (acid form) | 10 |
| DIATOMITE D30 | 75 |
| TALC T20A | 20 |
| Water (residual) | 5. |

This formulation now exhibited an acceptable level of foam and can be compared to that of Comparative Example 12.

Embodiment Example 19

An Ametryn 800 g/Kg WG formulation was made according to the following composition:

| Ametryn technical (98% w/w) | 816 g/Kg |
| --- | --- |
| TERSPERSE 2700 | 45 |
| TERWET 1004 | 18 |
| Sodium Stearate | 5 |
| EDTA (acid form) | 5 |
| AQUALIC DL 100 | 10 |
| DIATOMITE D30 | 81 |
| TALC T20A | 15 |
| Water (residual) | 5 |

This formulation exhibited an acceptable level of foam and can be compared to that of Comparative Example 12. The dispersion properties are not optimal, but this was found to be due to unmilled particles of active ingredient in this technical grade.

Embodiment Example 20

An Ametryn 800 g/Kg WG formulation was made according to the following composition:

| Ametryn technical (98% w/w) | 816 g/Kg |
| --- | --- |
| TERSPERSE 2700 | 45 |
| TERWET 1004 | 17 |
| Sodium Stearate | 5 |

-continued

| Ametryn technical (98% w/w) | 816 g/Kg |
|---|---|
| AQUALIC DL 100 | 10 |
| DIATOMITE D30 | 87 |
| TALC T20A | 15 |
| Water (residual) | 5. |

This formulation exhibited a reduced (and acceptable) level of foam compared to that of Comparative Example 12.

Embodiment Example 21

An atrazine 800 g/Kg wettable powder formulation was made with the following composition:

| Atrazine technical. (98% w/w) | 842 g/Kg |
|---|---|
| TERSPERSE 2425 | 30 |
| EMPICOL LXS 95/S | 30 |
| Sodium Stearate | 6 |
| EDTA (Acid) | 12 |
| Fumed silica | 80. |

TERSPERSE 2425 is an alkyl naphthalene sulphonate salt dispersant supplied by Huntsman LLC. EMPICOL LXS/95S is an alkylsulph(on)ate wetting agent supplied by Huntsman Corporation LLC. This formulation exhibited an acceptable level of foam and can be compared to that of Comparative Example 13.

Embodiment Example 22

An ametryn 800 g/Kg wettable powder formulation was made with the following composition:

| Ametryn technical 1(98% w/w) | 842 g/Kg |
|---|---|
| TERSPERSE 2425 | 30 |
| EMPICOL LXS 95/S | 7 |
| TERWET 1004 | 8 |
| Sodium Stearate | 5 |
| EDTA (Acid) | 10 |
| TALC T45-B | 98. |

TERSPERSE 2425 is an alkyl naphthalene sulphonate salt dispersant supplied by Huntsman LLC. EMPICOL LXS/95S is an alkylsulph(on)ate wetting agent supplied by Huntsman Corporation LLC. This formulation exhibited an acceptable level of foam and can be compared to that of Comparative Example 14.

Embodiment Example 23

An Atrazine 900 g/Kg WG formulation was made according to the following composition:

| Atrazine technical (98% w/w) | 918 g/Kg |
|---|---|
| TERSPERSE 2700 | 39 |
| TERSPERSE 2100 | 5 |
| TERWET 1004 | 15 |
| Sodium Stearate | 3.5 |
| EDTA (Acid) | 16.5 |
| Water (residual) | 3. |

The formulation exhibited an acceptable and very low level of foam. This can be compared to the results obtained for Comparative Examples 1, 2, 4 and 5. The technical used in this formulation was shown to have a high level of unmilled material leading to higher than desired level of retained material on dispersion. Comparative Example 1, was made again using this technical material, and showed similar levels. The formulation exhibited an acceptable level of dispersion performance compared to that of Comparative Example 3.

Embodiment Example 24

An Atrazine 900 g/Kg WG formulation was made according to the following composition:

| Atrazine technical (98% w/w) | 918 g/Kg |
|---|---|
| TERSPERSE 2700 | 39 |
| TERSPERSE 2100 | 5 |
| TERWET 1004 | 15 |
| Sodium Stearate | 3.5 |
| EDTA (Acid) | 12 |
| TALC T20A | 4.5 |
| Water (residual) | 3. |

The formulation exhibited an acceptable and very low level of foam. This can be compared to the results obtained for Comparative Examples 1, 2, 4 and 5. The technical used in this formulation was shown to have a high level of unmilled material leading to a higher than desired level of retained material on dispersion. Comparative Example 1, which was made using this technical material, showed similar levels. The formulation also exhibited an acceptable level of dispersion performance compared to that of Comparative Example 3.

Embodiment Example 25

An Atrazine 900 g/Kg WG formulation was made according to the following composition:

| Atrazine technical (98% w/w) | 918 g/Kg |
|---|---|
| TERSPERSE 2700 | 39 |
| TERSPERSE 2100 | 5 |
| TERWET 1004 | 15 |
| Sodium Stearate | 2 |
| EDTA (Acid) | 16.5 |
| TALC T20A | 1.5 |
| Water (residual) | 3. |

The formulation exhibited an acceptable and very low level of foam. This can be compared to the results obtained for Comparative Examples 1, 2, 4 and 5. The technical used in this formulation was shown to have a high level of unmilled material leading to higher than desired level of retained material on dispersion. Comparative Example 1, which was made using this technical material, showed similar levels. The formulation also exhibited an acceptable level of dispersion performance compared to that of Comparative Example 3.

Embodiment Example 26

An Atrazine 900 g/Kg WG formulation was made according to the following composition:

| Atrazine technical (98% w/w) | 918 g/Kg |
|---|---|
| TERSPERSE 2700 | 39 |
| TERSPERSE 2100 | 5 |

-continued

| Atrazine technical (98% w/w) | 918 g/Kg |
|---|---|
| TERWET 1004 | 15 |
| Sodium Stearate | 3.5 |
| EDTA (tetrasodium salt) | 16.5 |
| Water (residual) | 3. |

The formulation exhibited a reduced level of foam. This can be compared to the results obtained for Comparative Examples 1, 2, 4 and 5. However, this suggests the effectiveness of the EDTA tetra salt is reduced compared to the acid form. The technical used in this formulation was shown to have a high level of unmilled material leading to higher than desired level of retained material on dispersion. Comparative Example 3, which was made using this technical material, showed similar levels. The formulation also exhibited an acceptable level of dispersion performance compared to that of Comparative Example 3.

Embodiment Example 27

An Atrazine 900 g/Kg WG formulation was made according to the following composition:

| Atrazine technical. (98% w/w) | 918 g/Kg |
|---|---|
| TERSPERSE 2425 | 50 |
| SUPRAGIL WP | 15 |
| Atrazine technical. (98% w/w) | 918 g/Kg |
| Sodium Stearate | 4 |
| EDTA (Acid) | 10 |
| Water (residual) | 3. |

The desired foam height for this formulation is 25 mm after 1 minute. The result for this formulation may be compared to Comparative Example 16.

Embodiment Example 28

A metsulfuron 750 g/Kg WG formulation was made according to the following composition.

| Metsulfuron technical. (94% w/w) | 798 g/Kg |
|---|---|
| TERSPERSE 2700 | 45 |
| TERWET 1004 | 15 |
| TALC T20A | 20 |
| Sodium stearate | 4 |
| EDTA (Acid form) | 8 |
| AQUALIC DL100 | 10 |
| KINGWHITE 80 | 95 |
| Water (residual) | 5. |

The formulation exhibited an acceptable and very low level of foam. This can be compared to the results obtained for Comparative Example 17.

TABLE 3

Embodiment Example Results Summary

| Embodiment Example No. | Persistent Foaming (MT47.2) mm | | | Suspensibility (MT 15.2) | Wet Sieve Retention | | Static Wetting Time (MT 53.3.1) |
|---|---|---|---|---|---|---|---|
| | Int | 1 min | 2 min | % | 150 um % | 53 um % | |
| 1 | 30 | 6 | 4 | 90 | 0.002 | 0.120 | |
| 2 | 35 | 10 | 5 | 80 | 0.05 | 0.90 | |
| 3 | 40 | 30 | 28 | 93* | 0.021 | 0.32 | |
| 4 | 40 | 34 | 17 | 95 | 0.008 | 0.0437 | |
| 5 | 30 | 9 | 4 | 96 | 0.0004 | 0.0168 | |
| 6 | 20 | 15 | 12 | 94 | 0.06 | 0.181 | |
| 7 | 35 | 10 | 5 | 96 | 0.014 | 0.0748 | |
| 8 | 50 | 45 | 45 | 96 | 0.0037 | 0.0385 | |
| 9 | 45 | 40 | 38 | 85 | 0.0145 | 0.0290 | |
| 10 | 40 | 35 | 32 | 97 | 0.0008 | 0.02 | |
| 11 | 45 | 30 | 18 | 94 | 0.0068 | 0.034 | |
| 12 | 50 | 45 | 45 | 95 | 0.0126 | 0.0395 | |
| 13 | 42 | 42 | 40 | 86 | 0.009 | 0.1095 | |
| 14 | 42 | 38 | 35 | 84 | 0.0268 | 0.0915 | |
| 15 | 40 | 25 | 7 | 96 | 0.002 | 0.0292 | |
| 16 | 45 | 38 | 38 | 84 | 0.006 | 0.0558 | |
| 17 | 45 | 38 | 38 | 84 | 0.576 | 0.299 | |
| 18 | 45 | 40 | 36 | 87 | 1.61 | 1.15 | |
| 19 | 40 | 30 | 20 | 73 | 0.079 | 4.6 | |
| 20 | 40 | 40 | 35 | 76 | 0.11 | 1.04 | |
| 21 | 20 | 15 | 12 | 89 | 0.18 | 0.236 | 100 |
| 22 | 45 | 35 | 32 | 81 | 0.010 | 0.41 | 15 |
| 23 | 25 | 2 | 2 | 78 | 0.69 | 6.86 | |
| 24 | 41 | 18 | 4 | 73 | 0.61 | 8.26 | |
| 25 | 30 | 8 | 3 | 81 | 0.58 | 6.7 | |
| 26 | 47 | 45 | 45 | 82 | 0.16 | 7.7 | |
| 27 | 30 | 25 | 22 | 85 | 0.10 | 0.09 | |
| 28 | 22 | 3 | 2 | 80 | 0.13 | 1.0 | |

Embodiment Example 29

To the composition of Comparative Example 18 was added:

| | |
|---|---|
| Sodium stearate | 1% w/w |
| EDTA acid | 2 |
| AQUALIC DL 100 | 5 |

The persistent foaming performance was measured. Results: Int, 6 mm; 1 min, 5 mm; 2 min, 2 mm. The other properties of viscosity and antisettling behavior were found to be preserved.

Thus, a marked reduction in foam height was observed using this defoaming system. The result can be compared to that of Comparative Example 18. Presented in Tables 4-7 below is a summary of the composition of the Comparative and Embodiment Examples, respectively.

TABLE 4

| | | Comparative Example No. | | | | | | | | | | | | | |
|---|---|---|---|---|---|---|---|---|---|---|---|---|---|---|---|
| Ingredient Type | Ingredient | 1 | 2 | 3 | 4 | 5* | 6 | 7 | 8 | 9 | 10 | 11 | 12 | 13 | 14 |
| Active Ingredients | Atrazine 97% w/w | | | | | | | | | | | | | | 82.5 | |
| | Atrazine tech 98% w/w | 91.8 | 91.8 | 91.8 | 91.8 | 92.7 | | | | | | | | | | |
| | Simazine tech 98% w/w | | | | | | 91.8 | 91.8 | 91.8 | 91.8 | 91.8 | 91.8 | | | | |
| | Ametryn tech 97% w/w | | | | | | | | | | | | 82.5 | | | |
| | Ametryn 98% w/w | | | | | | | | | | | | | | | 84.2 |
| Wetting agents | TERWET 1004 | 1.6 | 1.6 | 1.6 | | 1.5 | 1.6 | | | 1.6 | 1.6 | 1.6 | 1.6 | | | 0.8 |
| | SUPRAGIL WP | | | | | | | 1.6 | | | | | | | | |
| | EMPIMIN OT-50 | | | | | | | | 3.2 | | | | | | | |
| | TERIC 168 | | | | 1.25 | | | | | | | | | | | |
| | EMPICOL LXS 95/S | | | | | | | | | | | | | | 2.0 | 0.7 |
| Fatty acid salt | Sodium Stearate | | | | | 0.5 | | | | | | 1.0 | | | | |
| Dispersing Agents | TERSPERSE 2700 | 4.2 | 4.2 | 4.2 | 3.75 | 4.2 | 3.6 | 3.6 | 3.6 | 3.6 | 3.6 | | 5.0 | | | |
| | TERSPERSE 2425 | | | | | | | | | | | | | | 3.0 | 3.0 |
| | TERSPERSE 2100 | 0.5 | | | | | | | | | | | | | | |
| Antifoam Agents | ANTIFOAM C | | | | | | | | | 0.5 | | | | | | |
| | FLUOWET PL80 | | | | 1.0 | | | | | | 0.5 | | | | | |
| | ANTIFOAM C on Tixosil | | 1.0 | | | | | | | | | | | | | |
| Inert fillers | TALC T20A | 1.4 | 1.0 | 1.0 | 2.7 | | 2.5 | 2.5 | 2.5 | 2.0 | 2.0 | 1.5 | | | | |
| | DIATOMITE D-30 | | | | | | | | | | | | 8.7 | | | |
| | Starch Powder | | | | 0.6 | | | | | | | | | | | |
| | TALC T-45B | | | | | | | | | | | | | 1.7 | 12.5 | 11.3 |
| | Water | 0.5 | 0.4 | 0.4 | 0.5 | 0.5 | 0.5 | 0.5 | 0.5 | 0.5 | 0.5 | 0.5 | 0.5 | | | |

TABLE 5

Summary of further Comparative Example Compositions

| | | Comparative Example No. | | |
|---|---|---|---|---|
| Ingredient type | Ingredient | 15 | 16 | 17 |
| Active ingredients | Atrazine 98% w/w | 91.8 | 91.8 | |
| | Metsulfuron-methyl 94% w/w | | | 79.8 |
| Wetting agent | TERWET 1004 | 1.5 | | 1.5 |
| | SUPRAGIL WP | | 1.5 | |
| Fatty acid salt | Sodium Stearate | | | |
| Dispersing agent | TERSPERSE 2700 | 3.9 | | 4.5 |
| | TERSPERSE 2100 | 0.5 | | |
| | TERSPERSE 2425 | | 6.0 | |
| Inert Fillers | TALC T20A | | 0.2 | 2.0 |
| | KINGWHITE 65 | | | 11.7 |
| Polymer | AQUALIC DL100 | 1.65 | | |
| Water | Residual water | 0.3 | 0.5 | 0.5 |

TABLE 6

Summary of Embodiment Example compositions

| | | Embodiment Example No. | | | | | | | | | | |
|---|---|---|---|---|---|---|---|---|---|---|---|---|
| Ingredient Type | Ingredient | 1 | 2 | 3 | 4 | 5 | 6 | 7 | 8 | 9 | 10 | 11 |
| Active Ingredients | Atrazine 97% w/w | | | | | | | | | | | |
| | Atrazine tech. (98% w/w) | 91.8 | 91.8 | 91.8 | | | | | | | | |

TABLE 6-continued

Summary of Embodiment Example compositions

| Type | Ingredient | | | | | | | | | | | |
|---|---|---|---|---|---|---|---|---|---|---|---|---|
| | Simazine tech (98% w/w) | | | | 91.8 | 91.8 | 91.8 | 91.8 | 91.8 | 91.8 | 91.8 | 91.8 |
| | Ametryn 95% w/w | | | | | | | | | | | |
| | Ametryn tech (98% w/w) | | | | | | | | | | | |
| | Ametryn tech (97% w/w) | | | | | | | | | | | |
| Wetting agents | TERWET 1004 | 1.5 | 1.5 | 1.5 | 1.6 | 1.6 | | | 1.6 | 1.6 | 1.6 | 1.6 |
| | SUPRAGIL WP | | | | | | 1.6 | | | | | |
| | EMPIMIN OT-50 | | | | | | | 3.2 | | | | |
| | EMPICOL LXS 95/S | | | | | | | | | | | |
| Dispersing Agent | TERSPERSE 2700 | 3.9 | 4.2 | 4.2 | 3.6 | 3.6 | 3.6 | 3.6 | 3.6 | 3.6 | 3.6 | 3.6 |
| | TERSPERSE 2100 | 0.5 | | | | | | | | | | |
| | TERSPERSE 2425 | | | | | | | | | | | |
| Fatty acid salts | Sodium Stearate | 0.35 | 0.4 | | 0.4 | 0.4 | 0.4 | 0.4 | | 0.4. | 0.4 | |
| | Sodium oleate | | | 0.4 | | | | | 0.4 | | | |
| | Sodium Laurate | | | | | | | | | 0.4 | | |
| Chelating agents | EDTA acid | 0.75 | 0.8 | 0.8 | 0.8 | 0.8 | 0.8 | 0.8 | 0.8 | 0.8 | | |
| | EDTA disodium salt | | | | | | | | | | 1.0 | |
| | NTA acid | | | | | | | | | | | 0.8 |
| | DEQUEST 2016 | | | | | | | | | | | |
| | Oxalic acid | | | | | | | | | | | |
| Polyacid polymer salts | AQUALIC DL 100 | 0.9 | | | 1.0 | 1.0 | 1.0 | 1.0 | 1.0 | | | |
| | Polyacrylic acid MW 2100 | | | | | | | | | | | |
| | Polyacrylic acid MW 5100 | | | | | | | | | | | |
| | PVA (MW 20,000) | | | | | | | | | | | |
| Fillers. | TALC T20A | | 0.8 | 0.8 | 1.3 | 0.3 | 0.3 | 0.3 | 0.3 | 0.3 | 1.1 | 1.3 |
| | Diatomite D 30 | | | | | | | | | | | |
| | TALC T45B | | | | | | | | | | | |
| | Absorptive silica | | | | | | | | | | | |
| | Water (residual) | 0.3 | 0.5 | 0.5 | 0.5 | 0.5 | 0.5 | 0.5 | 0.5 | 0.5 | 0.5 | 0.5 |

| Ingredient | | Embodiment Example No. | | | | | | | | | | |
|---|---|---|---|---|---|---|---|---|---|---|---|---|
| Type | Ingredient | 12 | 13 | 14 | 15 | 16 | 17 | 18 | 19 | 20 | 21 | 22 |
| Active Ingredients | Atrazine 97% w/w | | | | | | | | | | 82.5 | |
| | Atrazine tech. (98% w/w) | | | | | | | | | | | |
| | Simazine tech (98% w/w) | 91.8 | 91.8 | 91.8 | 91.8 | 91.8 | 91.8 | | | | | |
| | Ametryn 95% w/w | | | | | | | | | | | 84.2 |
| | Ametryn tech (98% w/w) | | | | | | | 82.5 | 81.6 | 81.6 | | |
| | Ametryn tech (97% w/w) | | | | | | | 82.5 | | | | |
| Wetting agents | TERWET 1004 | 1.6 | 1.6 | 1.6 | 1.6 | 1.6 | 1.6 | 1.0 | 1.8 | 1.7 | | 0.8 |
| | SUPRAGIL WP | | | | | | | | | | | |
| | EMPIMIN OT-50 | | | | | | | | | | | |
| | EMPICOL LXS 95/S | | | | | | | | | | 3.0 | 0.7 |
| Dispersing Agent | TERSPERSE 2700 | 3.6 | 3.6 | 3.6 | 3.6 | 3.6 | 3.6 | 5.0 | 4.5 | 4.5 | | |
| | TERSPERSE 2100 | | | | | | | | | | | |
| | TERSPERSE 2425 | | | | | | | | | | 3.0 | 3.0 |
| Fatty acid salts | Sodium Stearate | 0.4 | 0.4 | 0.4 | 0.4 | 0.4 | 0.4 | 0.5 | 0.5 | 0.5 | 0.6 | 0.5 |
| | Sodium oleate | | | | | | | | | | | |
| | Sodium Laurate | | | | | | | | | | | |
| Chelating agents | EDTA acid | | | | 0.8 | 0.8 | 0.8 | 1.0 | 0.5 | | 1.2 | 1.0 |
| | EDTA disodium salt | | | | | | | | | | | |
| | NTA acid | 0.8 | | | | | | | | | | |
| | DEQUEST 2016 | | 0.8 | | | | | | | | | |
| | Oxalic acid | | | 0.8 | | | | | | | | |

TABLE 6-continued

Summary of Embodiment Example compositions

| | | | | | | | | | | |
|---|---|---|---|---|---|---|---|---|---|---|
| Polyacid polymer salts | AQUALIC DL 100 | 1.0 | 1.0 | 1.0 | | | | 1.0 | 1.0 | |
| | Polyacrylic acid MW 2100 | | | | 1.0 | | | | | |
| | Polyacrylic acid MW 5100 | | | | | 1.0 | | | | |
| | PVA (MW 20,000) | | | | | | 1.0 | | | |
| Fillers. | TALC T20A | 0.3 | 0.3 | 0.3 | 0.3 | 0.3 | 0.3 | 2.0 | 1.5 | 1.5 |
| | Diatomite D 30 | | | | | | | 7.5 | 8.1 | 8.7 |
| | TALC T45B | | | | | | | | | 9.8 |
| | Absorptive silica | | | | | | | | 8.0 | |
| | Water (residual) | 0.5 | 0.5 | 0.5 | 0.5 | 0.5 | 0.5 | 0.5 | 0.5 | 0.5 |

TABLE 7

Summary of Further Embodiment Example Compositions

| | | Embodiment Example No. | | | | | |
|---|---|---|---|---|---|---|---|
| Ingredient type | Ingredient | 23 | 24 | 25 | 26 | 27 | 28 |
| Active ingredients | Atrazine 98% w/w | 91.8 | 91.8 | 91.8 | 91.8 | 91.8 | |
| | Metsulfuron-methyl 94% w/w | | | | | | 79.8 |
| Wetting agent | TERWET 1004 | 1.5 | 1.5 | 1.5 | 1.5 | | 1.5 |
| | SUPRAGIL WP | | | | | 1.5 | |
| Fatty acid salt | Sodium Stearate | 0.35 | 0.35 | 0.2 | 0.35 | 0.4 | 0.4 |
| Dispersing agent | TERSPERSE 2700 | 3.9 | 3.9 | 3.9 | 3.9 | | 4.5 |
| | TERSPERSE 2100 | 0.5 | 0.5 | 0.5 | 0.5 | | |
| | TERSPERSE 2425 | | | | | 5.0 | |
| Inert Fillers | TALC T20A | | 0.45 | 0.15 | | | 2.0 |
| | KINGWHITE 65 | | | | | | 9.5 |
| Chelate | EDTA acid | | 1.2 | 1.65 | | 1.0 | 0.8 |
| | EDTA Tetrasodium salt | | | | 1.65 | | |
| Polymer | AQUALIC DL100 | | | | | | 1.0 |
| Water | Residual water | 0.3 | 0.3 | 0.3 | 0.3 | 0.3 | 0.5 |

While preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The discussion of a reference herein is not an admission that it is prior art to the present invention, especially any reference that may have a publication date after the priority date of this application. The disclosures of all patents, patent applications, and publications cited herein are hereby incorporated by reference, to the extent that they provide exemplary, procedural or other details supplementary to those set forth herein.

The invention claimed is:

1. A solid agrochemical formulation comprising an agriculturally active agent and a defoaming composition comprising a fatty acid salt and a chelating agent, wherein a level of the defoaming composition is from about 0.1% w/w to about 20% w/w.

2. The formulation of claim 1 wherein the agriculturally active agent comprises herbicides, insecticides, fungicides, biocides, molluscicides, algaicides, plant growth regulators, anthelminthics, rodenticides, nematocides, acaricides, amoebicides, protozoacides, crop safeners, adjuvants, or combinations thereof.

3. The formulation of claim 1 wherein the agriculturally active agent comprises triazine, urea, or combinations thereof.

4. The formulation of claim 3 wherein the solid agrochemical formulation is in a WDG or WP formulation.

5. The formulation of claim 1 wherein the agriculturally active agent comprises atrazine, simazine, or combinations thereof.

6. The formulation of claim 1 wherein the fatty acid salt comprises $C_8$ to $C_{21}$ fatty acids.

7. The formulation of claim 1 wherein the fatty acid salt comprises sodium stearate, sodium oleate, aluminum stearate, or combinations thereof.

8. The formulation of claim 1 wherein the chelating agent comprises ethylene diamine tetraacetic acid, gluconic acid, nitrilotriacetic acid, diethylenetriamine pentaacetic acid, salts thereof, hydrates thereof or combinations thereof.

9. The formulation of claim 7 wherein the chelating agent comprises ethylene diamine tetraacetic acid.

10. The formulation of claim 1 wherein the ratio of fatty acid salt to chelating agent is from about 1:100 to about 100:1.

11. The formulation of claim 1 wherein the fatty acid salt and chelating agent are present in the ratio of about 1:1.5 to about 1:3.

12. The formulation of claim 1, wherein the defoaming composition further comprises a polyacid polymer.

13. The formulation of claim 12 wherein the polyacid polymer comprises sodium polyacrylate.

14. The formulation of claim 13 wherein the sodium polyacrylate has a molecular weight of from about 500 daltons to about 20,000 daltons.

15. The formulation of claim 12 wherein the ratio of polyacid polymer to fatty acid salt and chelating agent is from about 1:3 to about 1:1.

16. The formulation of claim 1 further comprising a wetting agent.

17. The formulation of claim 16 wherein the wetting agent is present in the formulation in amounts from about 1% w/w to about 3% w/w.

18. The formulation of claim 1 further comprising a dispersing agent.

19. The formulation of claim 1 wherein the formulation comprises a pH from about 4 to about 9.

20. The formulation of claim 1 wherein the formulation is in the form of a water dispersible granule or wettable powder.

21. The formulation of claim 15, wherein the sodium polyacrylate has a molecular weight of from about 2,100 daltons to about 3,500 daltons.

22. The formulation of claim 7, wherein the chelating agent comprises ethylene diamine tetraacetic acid, gluconic acid, nitrilotriacetic acid, diethylenetriamine pentaacetic acid, salts thereof, hydrates thereof or combinations thereof.

23. The formulation of claim 1, wherein the defoaming composition further comprises a sodium salt of a polyacrylic acid copolymer and a pH from about 6 to 7, and a level of the defoaming composition is from about 1.2 wt % to about 2.5 wt % of the formulation.

24. A suspension concentrate formulation comprising water and a solid agrochemical formulation comprising an agriculturally active agent and a defoaming composition comprising a fatty acid salt and a chelating agent, wherein a level of the defoaming composition in the agrochemical formulation is from about 0.1% w/w to about 20% w/w.

25. The formulation of claim 24 wherein the agriculturally active agent comprises atrazine, simazine, or combinations thereof.

26. The formulation of claim 24 wherein the fatty acid salt comprises $C_8$ to $C_{21}$ fatty acids.

27. The formulation of claim 24 further comprising a polyacid polymer.

28. A method for preparing an aqueous dispersion of an agriculturally active agent in solid form comprising the steps of:
(A) providing a composition comprising an agriculturally active agent and a defoaming composition comprising a fatty acid salt, a chelating agent, and a polyacid polymer; and
(B) dispersing the composition in water.

29. The method of claim 28 wherein the level of the defoaming composition is from about 0.1% w/w to about 20% w/w.

30. The method of claim 29 wherein the ratio of polyacid polymer to fatty acid salt and chelating agent is from about 1:50 to about 50:1.

31. The method of claim 30, wherein the polyacid polymer is added as a sodium salt having molecular weight less than about 10,000 daltons.

* * * * *